United States Patent [19]

Gaull

[11] Patent Number: 4,751,085

[45] Date of Patent: Jun. 14, 1988

[54] HUMAN NUTRITIONAL COMPOSITIONS CONTAINING TAURINE AND VITAMINS AND/OR MINERALS

[76] Inventor: Gerald E. Gaull, 420 E. 51st St., Apt. 5-B, New York, N.Y. 10022

[21] Appl. No.: 914,881

[22] Filed: Oct. 3, 1986

Related U.S. Application Data

[63] Continuation of Ser. No. 645,446, Aug. 29, 1984, Pat. No. 4,629,625.

[51] Int. Cl.$^4$ ............... A61K 33/30; A61K 33/26; A61K 31/355; A61K 31/34
[52] U.S. Cl. ........................ 424/145; 424/147; 514/458; 514/474; 514/905
[58] Field of Search ............ 424/145, 147; 514/474, 514/905, 458

[56] References Cited

U.S. PATENT DOCUMENTS

| | | | |
|---|---|---|---|
| 4,218,404 | 8/1980 | Feuer et al. | 260/944 |
| 4,226,884 | 10/1980 | Feuer | 424/112 |
| 4,303,692 | 12/1981 | Gaull | 426/580 |
| 4,324,743 | 4/1982 | Feuer et al. | 260/513 N |
| 4,497,800 | 2/1985 | Larson et al. | 424/180 |
| 4,499,076 | 2/1985 | Ohashi et al. | 424/143 |

OTHER PUBLICATIONS

Chem. Abst. 96:102804q–(1982)–Hayes.
Chem. Abst. 102:61114m (1985) Pasantes-Morales.
"Role of Vitamins in Taurine Synthesis from Sulfate by the Chick"–J. Nutri. 102:313–318–1972–Tomichek et al.

Primary Examiner—Douglas W. Robinson

[57] ABSTRACT

Vitamin compositions and/or nutritional mineral compositions containing taurine are provided either alone or in food products, suitable for consumption by human adults.

5 Claims, No Drawings

HUMAN NUTRITIONAL COMPOSITIONS CONTAINING TAURINE AND VITAMINS AND/OR MINERALS

This is a continuation of application Ser. No. 645,446, filed Aug. 29, 1984, now U.S. Pat. No. 4,629,625.

This invention relates to taurine-containing compositions and the utilization of said compositions for human nutritional purposes. This invention also relates to vitamin and/or mineral-containing compositions useful as nutritional supplements for humans. These compositions can be employed per se as nutritional supplements or incorporated into a comestible, liquid and/or solid, for human consumption.

BACKGROUND OF THE INVENTION

Taurine has been suggested as a component in animal feed, see U.S. Pat. No. 3,636,195. Taurine has also been suggested for incorporation into synthetic infant formulas, see G. E. Gaull U.S. Pat. No. 4,303,692.

Taurine (2-aminoethanesulfonic acid, $NH_2CH_2CH_2SO_3H$) is a betasulfonic acid present in high concentrations in animal cells. Taurine and its related compounds, such as hypotaurine (2-aminoethanesulfinic acid) and isethionic acid (2-hydroxyethanesulfonic acid) are formed in animal tissue and vary in concentration from species to species and among tissues. Little, if any, taurine is found in plants.

Additionally, platelets and lymphocytes are found to have present large concentrations of taurine, ranging up to about 50% of the total pool of free amino acids present in these cells. The physiological function of taurine remains unclear, although it is clear that it is an important amino acid for maximal cell viability and homeostasis. Additionally, at least one investigator has termed taurine a "conditionally essential nutrient" meaning that, although the nutrient is not essential for normal subjects, certain individuals, having lost the ability to conserve the compound or having increased requirements due to illness or for other reasons, must supplement their diets with taurine to maintain normal health. Chipponi et al, *Am. J. Clin. Nut.*, 35, (May 1982), pp. 1112–1116; Jacobsen and Smith, *Phys. Rev.* v. 48, No. 2, (April 1968), pp. 424–511.

The cells of many species possess considerable ability to synthesize taurine, although this is not the case with primates, including man. Certain animals including primates and man have very limited ability to synthesize the amino acid, and rely on diet to maintain taurine stores.

Human B-lymphoblastoid cells take up taurine present in physiological concentrations in plasma, using an active uptake system. These same cells take up taurine when cultured in media supplemented with serum, and show progressive depletion of taurine when cultivated in chemically defined, taurine free media.

Taurine exhibits a positive effect on the number of viable cells in a culture when added to a taurine free medium used in such a culture. Evidence is available which supports the hypothesis that taurine mediates protective action on cell membranes which lead to an increase in cell viability. Huxtable and Bressler, *Biochem et Biophys. Acta.*, 323 (1973), pp. 573–583.

Retinols, the major components of vitamin A, and the related compounds, retinoids, are well known as inhibitors of cell growth. These compounds interact directly with membranes causing increases in permeability and fluidity, and destabilize biological membranes, Stillwell and Bryant, *Biochim et Biophys. Acta*, 731 (1983) 483–486. This results in hemolysis in erythrocytes, and in increased enzyme secretion in lysosomes. Additionally, when retinols are incorporated into lipid bilayers of liposomes, these are made more permeable to cations and to larger molecules, such as glycine, lysine and glucose. The increase in permeability is often accompanied by decreases in phase temperatures of the liposomes, as well as electrical resistance of the membranes.

Ascorbic acid, i.e. vitamin C, and the related ascorbates, in systems with iron compounds, are known to induce lipid peroxidation of cell membranes, see, e.g. Lewis, *Biochem. Pharm.* v. 33, No. 11, pp. 1705–14 (1984). The damage that results from this peroxidation is often accompanied by increased membrane permeability, and enhanced water accumulation. When either retinols or iron-ascorbate systems are present, cell viability is decreased due to membrane interference caused by the presence of these, Stillwell and Bryant, op. Cit.; Lewis, op. Cit.

Each of these, i.e. vitamin A (retinol), vitamin C (ascorbic acid or ascorbate), and iron compounds is a necessary nutrient for humans. Hence, removal of these substances from the diet is not possible. In fact, each of these substances may be taken not only through natural occurrence in comestibles, but also through vitamin and mineral nutritional supplements. These supplements are available in a variety of formulations, and often contain well in excess of the amount of each substance necessary for proper nutrition, even when suggested doses are taken. Many who take vitamin supplements, however, believe that increased consumption of these supplements will result in increased beneficial effects. Actually, such increased consumption may lead to increased risk of cell damage, as set forth herein.

Taurine and its physiologically acceptable derivatives have been shown to have a positive effect on cell viability, see, e.g. Alvarez and Storey, *Biol. Reprod.*, 29, 548–555 (1983). Evidence supports the view that taurine mediates a protective effect on cell membranes. Zinc has been shown to exhibit a protective effect on cell membranes as well.

Vitamin E, or tocopherol, is known as having positive effects in counteracting membrane destabilizing actions of retinoids, Stillwell and Bryant, op. Cit.; I. Gery, *Inv. Ophthal & Vis. Sci.* v. 19 (December 1980) pp. 751–759.

Hence, it is one object of this invention to prepare vitamin compositions having improved nutritional properties.

It is another object of this invention to provide comestibles or food compositions having improved nutritional properties.

How these, as well as other objects of this invention are realized, will be made clear in light of the following disclosure.

SUMMARY OF THE INVENTION

Taurine and its physiologically acceptable derivatives or related compounds are beneficial in maintaining cell homeostasis in humans and animals. Taurine, either alone or together with vitamin E compounds, such as tocopherols, and/or zinc compounds, hinder cell damage caused by vitamin A compounds, such as retinols, and vitamin C compounds, such as ascorbic acid, when the latter is present with iron compounds. Administration of taurine or its physiologically equivalent derivatives or related compounds, either alone or with either vitamin E compounds or zinc compounds, or both, is most readily accomplished by preparing vitamin compositions containing these, together with the vitamin A compounds and/or the vitamin C and iron combination whose affect they inhibit. Such compositions may be prepared in any of the standard ways in which vitamin compositions are prepared, such as pills, capsules and liquids, such as intravenous fluids, or may be incorporated in various comestibles, such as dairy or grain products. Additionally, taurine and its derivatives, along or with vitamin E compounds, or zinc compounds, or with both of these, stabilizes vitamin compositions containing vitamin A, and/or vitamin C and iron compounds.

Vitamin compositions in accordance with this invention comprise or consist essentially of vitamin A and taurine, vitamin C and taurine, vitamin E and taurine and combinations of the above. Nutritional supplements containing taurine are also useful, such as a nutritional supplements containing a physiologically acceptable zinc compound and taurine, a physiologically acceptable iron compound and taurine and combinations thereof alone or with other "minerals", such as a calcium and/or phosphorus compound beneficial for nutrition and health.

DETAILED DESCRIPTION OF THE INVENTION

Various mechanisms and models have been suggested to explain why taurine, alone or with either vitamin E, zinc, or both, stabilizes cell membranes and increases cell viability.

It appears that taurine effectively reverses the inhibition of cell viability caused by excess vitamin A, and iron-ascorbate systems. Additionally, taurine may be combined, either with vitamin E or zinc compounds, to even further reverse inhibition of cell viability caused by vitamin A or iron ascorbate systems.

The usefulness of taurine as an inhibitor of vitamin A and iron-ascorbate related cell damage is best applied in the preparation of vitamin compositions. Many vitamin compositions contain either vitamin A, or iron-ascorbate systems. The following examples support this.

EXAMPLE 1

The contents of the multi-vitamin preparation NATURE'S BOUNTY 1 TM, is as follows:

| Vitamin or Mineral | Amount | & U.S. RDA |
|---|---|---|
| Vitamin A | 25,000 IU | 500 |
| Vitamin D | 800 IU | 200 |
| Vitamin E | 30 IU | 100 |
| Vitamin C | 250 mg | 417 |
| Vitamin B-1 | 25 mg | 1667 |
| Vitamin B-2 | 25 mg | 1471 |
| Vitamin B-6 | 50 mg | 2500 |
| Vitamin B-12 | 50 mcg | 833 |
| Niacinamide | 50 mg | 250 |
| Calcium Pantothenate | 50 mg | 500 |
| Folic Acid | 400 mcg | 100 |
| Biotin | 50 mcg | 17 |
| Choline | 15 mg | (none given) |
| Inositol | 15 mg | (none given) |
| Paba | 50 mg | (none given) |
| Vitamin K | 10 mcg | (none given) |
| Iodine | 150 mcg | 100 |
| Iron | 10 mg | 56 |
| Calcium | 50 mg | 5 |
| Phosphorus | 23 mg | 2 |
| Chromium | 100 mcg | (none given) |
| Magnesium | 100 mg | 25 |
| Zinc | 15 mg | 100 |
| Manganese | 5 mg | (none given) |
| Selenium | 25 mcg | (none given) |
| Copper | 2 mg | 100 |
| Potassium | 1 mg | (none given) |
| Chloride | 1 mg | (none given) |
| Molybdenum | 15 mcg | (none given) |

EXAMPLE 2

The constituents of VITA-LEA® multivitamin and multimineral supplements, a product of SHAKLEE Corporation, are as follows:

| Vitamin or Mineral | Quantity | % U.S. RDA |
|---|---|---|
| Vitamin A | 5000 IU | 100% |
| Vitamin D | 400 IU | 100 |
| Vitamin E | 30 IU | 100 |
| Vitamin C | 90 mg | 150 |
| Folic Acid | 0.4 mg | 100 |
| Thiamine | 2.1 mg | 140 |
| Riboflavin | 2.4 mg | 140 |
| Niacin | 20 mg | 100 |
| Vitamin $B_6$ | 2 mg | 100 |
| Vitamin $B_{12}$ | 9 mcg | 150 |
| Biotin | 0.3 mg | 100 |
| Pantothenic Acid | 10 mg | 100 |
| Calcium | 0.6 g | 60 |
| Phosphorus | 0.45 g | 45 |
| Iodine | 150 mcg | 100 |
| Iron | 18 mg | 100 |
| Magnesium | 200 mg | 50 |
| Copper | 2 mg | 100 |
| Zinc | 15 mg | 100 |

EXAMPLE 3

The following are the guidelines of the Expert Panel of the Nutrition Advisory Group, AMA Department of Foods and Nutrition (December 1975), for formulations for intravenously administered vitamins:

| Vitamin | Infants/Children (Under 11 years) | Adult |
|---|---|---|
| Vitamin A | 2300 IU | 3,300 IU (66%) |
| Vitamin D | 400 IU | 200 IU (50%) |
| Vitamin E | 7.0 IU | 10.0 IU (33%) |
| Vitamin K | 0.2 mg | — |
| Ascorbic Acid | 80.0 mg | 100 mg (140%) |
| Folacin | 140 mcg | 400 mg |
| Niacin | 17.0 mg | 40.0 mg (200%) |
| Riboflavin | 1.4 | 3.6 mg (210%) |
| Thiamine | 1.2 | 3.0 mg (200%) |
| Vitamin $B_6$ | 1.0 mg | 4.0 mg (200%) |
| Vitamin $B_{12}$ | 1.0 mcg | 5.0 mcg (100%) |
| Pantothenic Acid | 5.0 mg | 15.0 mg (150%) |
| Biotin | 20.0 mcg | 60.0 mcg (200%) |

(No U.S. RDA percentages are given for children as the recommended amounts vary over the age span given).

EXAMPLE 4

A high potency vitamin supplement prepared by Lederle Laboratories and sold under the registered trademark CENTRUM has the following composition.

| Ingredient | Quantity | % U.S. RDA |
|---|---|---|
| Vitamin A | 5000 I.U. | 100 |
| Vitamin E | 30 I.U. | 100 |
| Vitamin C | 90 mg | 150 |
| Folic Acid | 400 mcg | 100 |
| Vitamin $B_1$ | 2.25 mg | 150 |
| Vitamin $B_2$ | 2.6 mg | 153 |
| Niacinamide | 20 mg | 100 |
| Vitamin $B_6$ | 3 mg | 150 |
| Vitamin $B_{12}$ | 9 mcg | 150 |
| Vitamin D | 400 I.U. | 100 |
| Biotin | 45 mcg | 15 |
| Pantothenic Acid | 10 mg | 100 |
| Calcium | 162 mg | 16 |
| Phosphorus | 125 mg | 13 |
| Iodine | 150 mcg | 100 |
| Iron | 27 mg | 150 |
| Magnesium | 100 mg | 25 |
| Copper | 3 mg | 150 |
| Manganese | 7.5 mg | Not Established |
| Potassium | 7.7 mg | Not Established |
| Chloride | 7 mg | Not Established |
| Chromium | 15 mcg | Not Established |
| Molybdenum | 15 mcg | Not Established |
| Selenium | 25 mcg | Not Established |
| Zinc | 22.5 mg | 150 |

EXAMPLE 5

The prenatal vitamin supplement for use by pregnant and lactating mothers, produced by Lederle Laboratories and sold under the trademark MATERNA, has the following composition.

| Ingredient | Quantity | % U.S. RDA |
|---|---|---|
| Vitamin A | 8000 I.U | 100 |
| Vitamin D | 400 I.U. | 100 |
| Vitamin E | 30 I.U. | 100 |
| Vitamin C | 100 mg | 167 |
| Folic Acid | 1 mg | 125 |
| Thiamine (Vitamin $B_1$) | 3 mg | 224 |
| Riboflavin (Vitamin $B_2$) | 3.4 mg | 170 |
| Vitamin $B_6$ | 4 mg | 160 |
| Niacinamide | 20 mg | 100 |
| Vitamin $B_{12}$ | 12 mcg | 150 |
| Calcium | 250 mg | 19 |
| Iodine | 0.3 mg | 200 |
| Iron | 60 mg | 333 |
| Magnesium | 25 mg | 6 |
| Copper | 2 mg | 100 |
| Zinc | 25 mg | 167 |
| Docusate Sodium | 50 mg | Not Established |

In each of Examples 1–5 it is possible to add taurine to these vitamin compositions as an additional or supplemental ingredient. The exceptional large amounts of vitamins A and C in each of these vitamin compositions, taken with the usual practice that many vitamin compositions are taken on a daily basis, indicates that taurine is usefully added to or incorporated in these vitamin compositions to inhibit the effect of any excess these vitamins (vitamins A and C) have on cell viability.

The taurine used in such vitamin compositions may be in the form of the compound itself or any of its salts or other derivative forms which are physiologically acceptable and equivalent. Vitamin E and zinc, along with taurine, also may be added in the form of any of their derivatives which are physiologically acceptable. Formulations containing these substances may vary in the amounts and proportions of the substances therein.

For example, in parts by weight or moles, suitable ranges may be:

| Vitamin or Mineral | Amount (ppw or moles) |
|---|---|
| Vitamin A | 0.01–10 |
| Iron | 0.01–10 |
| Vitamin C | 0.01–30 |
| Taurine | 0.01–30 |
| Vitamin E | 0–80 |
| Zinc | 0–30 | and in percentages by weight:

| Vitamin or Mineral | pct. by weight or moles |
|---|---|
| Vitamin A | 1–20 |
| Iron | 1–20 |
| Vitamin C | 1–20 |
| Taurine | 1–20 |
| Vitamin E | 0–20 |
| Zinc | 0–20 |

The composition of vitamins and minerals as described may be prepared in any of the forms associated with vitamin supplements, such as solids, including but not limited to pills, capsules, and particle forms, and liquids, such as syrups, and preparations suitable for intravenous intake.

The vitamin compositions, as described, may also be incorporated with comestibles and consumed. Many comestibles are enriched by the addition of vitamin supplements thereto, such as enriched breads, ready to eat cereals, and other grain or farinaceous products, as are dairy products, such as breakfast beverages comprising milk and flavored or unflavored milk additives and the like.

Usually, the vitamin and/or mineral compositions of this invention are suitable for self administration, such as in the case of vitamin and/or mineral pills and enriched comestibles. Where, however, the composition is not sutable for self administration, such as in the case of intravenous administration of vitamin supplements, the taurine and either vitamin E or zinc or both may be added separately by the administrator of the supplement or shortly before administration.

As indicated hereinabove, taurine appears to be important for human well being. In accordance with one aspect of this invention, taurine for this purpose is best utilized or administered together with a vitamin, such as vitamin A, vitamin C, vitamin D, vitamin E and/or a B vitamin. Taurine is also usefully administered or taken together with a nutritional supplement, such as a mineral, such as a physiologically acceptable phosphate, calcium compound, chromium compound, magnesium compound, zinc compound, manganese compound, selenium compound, copper compound, potassium compound, a chloride and/or a molybdenum compound. If desired, a composition can also be prepared in accordance with the practices of this invention containing taurine, together with a vitamin, such as those mentioned hereinabove, and a mineral, such as those mentioned hereinabove. These mineral containing compositions may be in liquid or solid (pill, capsule or powder) form or may be included in a food prepared for adult consumption, such as a liquid beverage or solid comestible as a nutritional and/or vitamin supplement therein.

The taurine-containing compositions of this invention, where desirable or necessary, might also include a suitable excipient, which excipient may have a nutritional benefit, as indicated hereinabove, such as a dairy or dairy-like beverage fortified or enriched with compositions of this invention. These taurine-containing compositions, as indicated, may be in liquid form or solid, finely divided form or may be incorporated in conventional well known food materials, e.g. yogurt, drink mixes, spreads, concentrated beverages, peanut butter, margarine, sweetening compositions, synthetic or natural, such as sugar syrups, low calorie synthetic sweetener compositions and the like. As indicated, the practices of this invention may be advantageously utilized in substantially any aspect or use wherein vitamins and/or minerals are incorporated in foods. The important aspect of this invention resides in the utilization of taurine in compositions containing other vitamin and/or nutritional mineral supplements or compositions to provide improved nutrition.

Examples of vitamin compositions and/or nutritional mineral-containing supplements in accordance with this invention are such compositions which contain or consist essentially of about 10-100 milligrams or parts by weight or moles vitamin E and 10-1000 milligrams or parts by weight or moles taurine. When such compositions are expressed in parts by weight or moles, the parts by weight taurine relative to vitamin E in said compositions are based on the total parts by weight or moles taurine and vitamin E in said compositions. Similar such compositions are provided containing or consisting essentially of taurine and vitamin C, taurine and vitamin A, taurine and a B vitamin and taurine and vitamin D and taurine, including compositions containing more than one of the aforesaid vitamins and compositions containing taurine and one or more of the aforesaid minerals and compositions containing taurine and a combination of one or more of the aforesaid vitamins and minerals.

What is claimed is:

1. A vitamin composition in liquid form consisting essentially of about 0.1-10 parts by weight or moles of vitamin A, about 0.01-10 parts by weight or moles of an iron compound, about 0.01-10 parts by weight or moles of vitamin C, about 0.01-30 parts by weight or moles of taurine, about 0-80 parts by weight or moles of vitamin E and about 0-30 parts by weight or moles of a zinc compound.

2. A liquid vitamin composition consisting essentially of about 1-20% by weight or moles of vitamin A, about 1-20% by weight or moles vitamin C, about 1-20% by weight or moles of an iron compound and about 1-20% by weight or moles of taurine.

3. A liquid vitamin composition in accordance with claim 2 further comprising about 1-20% by weight of vitamin E.

4. A liquid vitamin composition in accordance with claim 2 further comprising about 1-20% by weight or moles of a zinc compound.

5. A liquid vitamin composition in accordance with claim 2 further comprising about 0-20% by weight or moles of vitamin E and about 0-20% by weight or moles of a zinc compound.

* * * * *